(12) United States Patent
McManus

(10) Patent No.: US 6,490,083 B1
(45) Date of Patent: Dec. 3, 2002

(54) MICROSCOPY METHOD AND APPARATUS

(76) Inventor: Dennis Q. McManus, 405 Tecumseh, Springfield, IL (US) 62704

(*) Notice: Subject to any disclaimer, the term of this patent is extended or adjusted under 35 U.S.C. 154(b) by 0 days.

(21) Appl. No.: 09/576,502

(22) Filed: May 23, 2000

Related U.S. Application Data

(63) Continuation of application No. 09/150,113, filed on Sep. 9, 1998, now abandoned.

(51) Int. Cl.⁷ .............................. G09B 21/22; A61B 1/06
(52) U.S. Cl. ...................... 359/376; 359/368; 359/435; 600/164; 600/167
(58) Field of Search ................................ 359/368–390; 600/109, 112, 160–168, 174, 183, 142

(56) References Cited

U.S. PATENT DOCUMENTS

| | | | |
|---|---|---|---|
| 2,102,274 A | | 12/1937 | Larimore .................... 359/385 |
| 3,556,085 A | | 1/1971 | Takahashi ................... 600/129 |
| 3,769,963 A | | 11/1973 | Goldman et al. ........... 600/476 |
| 3,941,121 A | | 3/1976 | Olinger et al. .............. 600/167 |
| 4,319,563 A | | 3/1982 | Kubota ....................... 600/129 |
| 4,364,629 A | | 12/1982 | Lang et al. .................. 359/377 |
| 4,566,438 A | | 1/1986 | Liese et al. ................. 600/176 |
| 4,569,333 A | | 2/1986 | Bel et al. .................... 600/166 |
| 4,623,789 A | | 11/1986 | Ikeda et al. ................. 250/227 |
| 4,624,243 A | | 11/1986 | Lowery et al. ............. 600/313 |
| 4,658,825 A | | 4/1987 | Hochberg et al. .......... 600/313 |
| 4,664,486 A | | 5/1987 | Landre et al. ............... 359/435 |
| 4,795,434 A | | 1/1989 | Kujawski .................... 604/159 |
| 4,877,016 A | | 10/1989 | Kantor et al. ............... 600/313 |
| 4,905,082 A | * | 2/1990 | Nishigaki et al. ............. 358/98 |
| 4,913,151 A | | 4/1990 | Harui et al. ................. 600/313 |
| 5,095,887 A | | 3/1992 | Leon et al. .................. 359/368 |
| 5,199,417 A | | 4/1993 | Muller et al. ............... 600/128 |
| 5,270,855 A | * | 12/1993 | Hasegawa ................... 359/368 |
| 5,271,380 A | | 12/1993 | Riek et al. .................. 600/164 |
| 5,295,477 A | | 3/1994 | Janfaza ....................... 600/142 |
| 5,396,366 A | * | 3/1995 | Brown et al. ............... 359/435 |
| 5,431,151 A | | 7/1995 | Riek et al. .................. 600/164 |
| 5,496,261 A | * | 3/1996 | Sander ........................ 600/163 |
| 5,612,816 A | * | 3/1997 | Strahle et al. .............. 359/376 |
| 5,630,784 A | | 5/1997 | Siegmund et al. .......... 359/376 |
| 5,632,718 A | * | 5/1997 | Igarashi et al. ............. 600/160 |
| 5,702,350 A | | 12/1997 | Vry et al. .................... 600/166 |
| 5,785,704 A | * | 7/1998 | Bille et al. .................... 606/17 |
| 5,800,165 A | * | 9/1998 | Kirsch et al. ................. 433/29 |

FOREIGN PATENT DOCUMENTS

| | | |
|---|---|---|
| DE | 1616107 | 4/1971 |

OTHER PUBLICATIONS

NSG America, Inc., SELFOC® Product Guide, published before Sep. 9, 1998, p. 22.
NSG America, Inc., SELFOC Lens Array (SLA) Reference Book, published before Sep. 9, 1998, pp. 1–4.
P.M. Delaney et al.,Handbook of Biological Confocal Microscopy, published before Sep. 9, 1998, pp. 515–523.

* cited by examiner

*Primary Examiner*—Thong Nguyen
(74) *Attorney, Agent, or Firm*—Senniger, Powers, Leavitt & Roedel

(57) ABSTRACT

An assembly for viewing cells inside tissue of a living organism. The assembly includes a confocal microscope having an objective for magnifying an image positioned at a focal plane of the objective and a light source adapted to direct light through the objective. The assembly also includes a rigid elongate tube extending from the objective to a tip sized and shaped for penetrating the tissue of the living organism. The tube has a hollow interior aligned with the objective. The interior of the tube is free of fiberoptic bundles and cover glasses. The assembly also includes a unitary cylindrical lens positioned in the hollow interior of the tube for transmitting light from the light source to the cells inside the tissue of the living organism adjacent the tip to illuminate the cells. The lens has a focal plane adjacent the tip positioned at a location corresponding to the illuminated cells, an image plane opposite the tip positioned at the focal plane of the microscope objective and a sufficient resolution for transmitting an image of the illuminated cells positioned at the focal plane of the lens to the focal plane of the objective.

28 Claims, 5 Drawing Sheets

MICROSCOPY METHOD AND APPARATUS

CROSS-REFERENCE TO RELATED APPLICATION

This is a continuation of U.S. patent application Ser. No. 09/150,113 filed Sep. 9, 1998 now abandoned.

BACKGROUND OF THE INVENTION

The present invention relates to microscopes, and more particularly, to methods and apparatus for viewing and manipulating cells inside living tissue with a microscope.

Before tissue can be viewed using conventional microscopes, it must usually be removed from its host organism, especially when features below the surface of the tissue are viewed. However, living tissue cannot survive long after removal from its host without sophisticated support equipment. Further, the tissue may change if the support equipment does not precisely duplicate its natural environment. Although a few conventional microscopes (e.g., surgical microscopes) have been designed to view living tissue without removing it from its host, these microscopes have limited resolution. Therefore, small features cannot be seen with these microscopes.

Due to the inherent limitations of conventional microscopes, many features of living tissue have not been viewed directly. For instance, physical changes in the human brain resulting from internal processes have not been viewed at the cellular level. As a result, information such as how quickly connections (e.g., synapse connections) are made and lost within the brain is unknown. Further, viewing removed brain tissue does not permit clear understanding of these processes because complex behavior (e.g., speech or learning) cannot be studied when the tissue is removed from its host. The inability of conventional microscopes to view brain cell connections is particularly frustrating because it is envisioned that viewing these connections could answer questions concerning the causes of brain dysfunction such as Alzheimer's disease.

One of the reasons tissue must be removed from its host before it may be viewed by most conventional microscopes is that the tissue must be highly illuminated to be seen through the microscopes. Confocal optical microscopes eliminate this problem by illuminating the tissue with a laser aimed at the tissue through the lens of the microscope. These microscopes make it possible to view an object without an external illumination source. However, conventional confocal optical microscopes cannot view more than a very short distance (i.e., about 200 nm) below the surface of the tissue. Thus, deeper tissue cannot be viewed without separating the tissue from the living organism.

Conventional microscopes and methods of use have other disadvantages which limit their usefulness when viewing tissue inside a host. For instance, stains are ordinarily applied to tissue before being viewed with microscopes to improve the optical attributes of features within the tissue. However, the amount of stain used to produce suitable optical attributes frequently kills or injures cells in the tissue and sometimes harms the host. Therefore, conventional methods of applying stain are generally not appropriate when examining living tissue inside a host organism.

SUMMARY OF THE INVENTION

Among the several objects and features of the present invention may be noted the provision of a microscope attachment capable of viewing internal features of tissue without removing the tissue from its host; the provision of a microscope which enables small amounts of stains and/or other fluids to be precisely directed toward a particular site in tissue within the field of view of the microscope; the provision of a microscope capable of precisely positioning instruments for manipulation of tissue within the field of view of the microscope; and the provision of a microscope having a fluid delivery system which delivers fluid to a site within the field of view of the microscope in amounts which are effective and substantially nontoxic.

Briefly, apparatus of this invention is an assembly for viewing cells inside tissue of a living organism. The assembly includes a confocal microscope having an objective for magnifying an image positioned at a focal plane of the objective and a light source adapted to direct light through the objective. The assembly also includes a rigid elongate tube extending from the objective to a tip sized and shaped for penetrating the tissue of the living organism. The tube has a hollow interior aligned with the objective. The interior of the tube is free of fiberoptic bundles and cover glasses. The assembly also includes a unitary cylindrical lens positioned in the hollow interior of the tube for transmitting light from the light source to the cells inside the tissue of the living organism adjacent the tip to illuminate the cells. The lens has a focal plane adjacent the tip positioned at a location corresponding to the illuminated cells, an image plane opposite the tip positioned at the focal plane of the microscope objective and a sufficient resolution for transmitting an image of the illuminated cells positioned at the focal plane of the lens to the focal plane of the objective.

In another aspect, the invention includes an attachment for use with a microscope. The attachment includes a rigid elongate tube having a hollow interior extending to a tip having a width of less than about three millimeters to permit the tip to be inserted into tissue of a living organism. The attachment further comprises a unitary cylindrical lens positioned in the hollow interior of the tube for transmitting an image of a specimen positioned at a focal plane of the lens adjacent a front end thereof to an image plane of the lens adjacent a rear end thereof opposite said front end. The lens is free of fiberoptic bundles and cover glasses between the focal plane of the lens and the image plane of the lens. The lens has a sufficient resolution to permit cells of the tissue to be viewed through the lens with a microscope. The attachment also has a mount for mounting the tube and lens on a microscope in a position wherein the image plane of the lens corresponds with a focal plane of the microscope objective.

In yet another aspect, the invention includes a method of viewing cells inside tissue of living organisms. The method comprises the steps of mounting a cylindrical lens adjacent an objective of a microscope and adjusting the lens so an image plane of the lens corresponds with a focal plane of the microscope objective. The lens and the objective are simultaneously moved as a unit to penetrate the tissue and position the lens so the cells lie within a focal plane of the lens.

Other objects and features of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION OF THE PREFERRED EMBODIMENT

Figure 1:
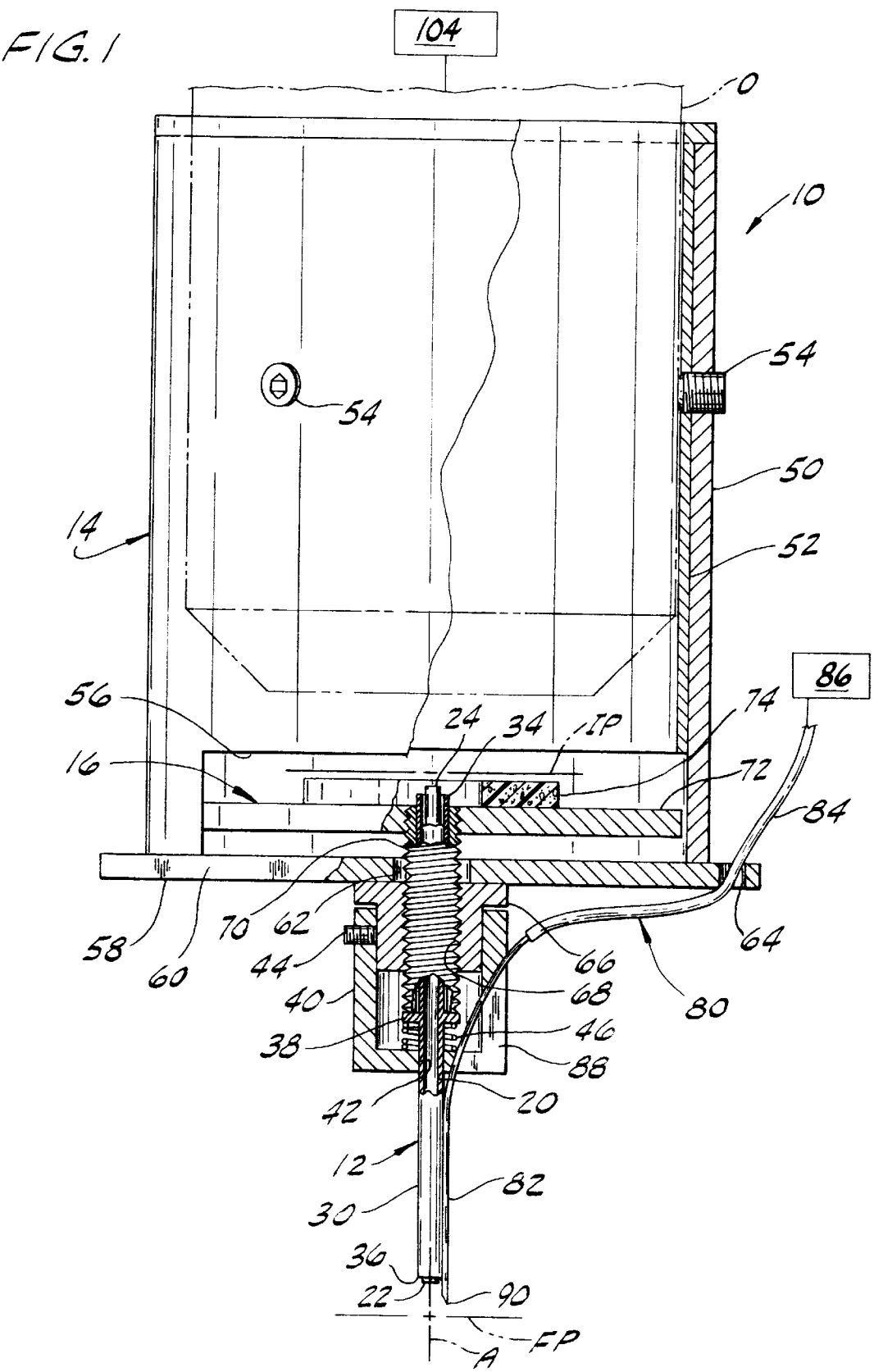
FIG. 1 is an elevation in partial section of a microscope attachment of the present invention.

Referring now to the drawings and in particular to FIG. 1, an attachment for use with a microscope is designated in its entirety by the reference numeral 10. The attachment 10 generally comprises a lens assembly, a mount and a focusing mechanism, generally designated 12, 14 and 16, respectively.

The lens assembly 12 includes a unitary cylindrical lens or microlens 20 such as a Selfoc® microlens having a small diameter, (e.g., less than about 3.0 mm). Selfoc is a federally registered trademark of Nippon Sheet Glass Co., Ltd. of Osaka, Japan. Selfoc® microlenses are available through NSG America, Inc. of Somerset, N.J. The microlens 20 transmits an image of a specimen (not shown) positioned at a focal plane FP of the microlens adjacent its front or lower end 22 to an image plane IP of the microlens adjacent a rear or upper end 24. As will be understood by those skilled in the art, the microlens is a unitary cylindrical lens having a diameter less than about 3 mm, and more preferably less than about 0.5 mm, having an objective lens portion 26 (FIG. 4) and a rlay lens portion 28 (FIG. 4).

Figure 4:
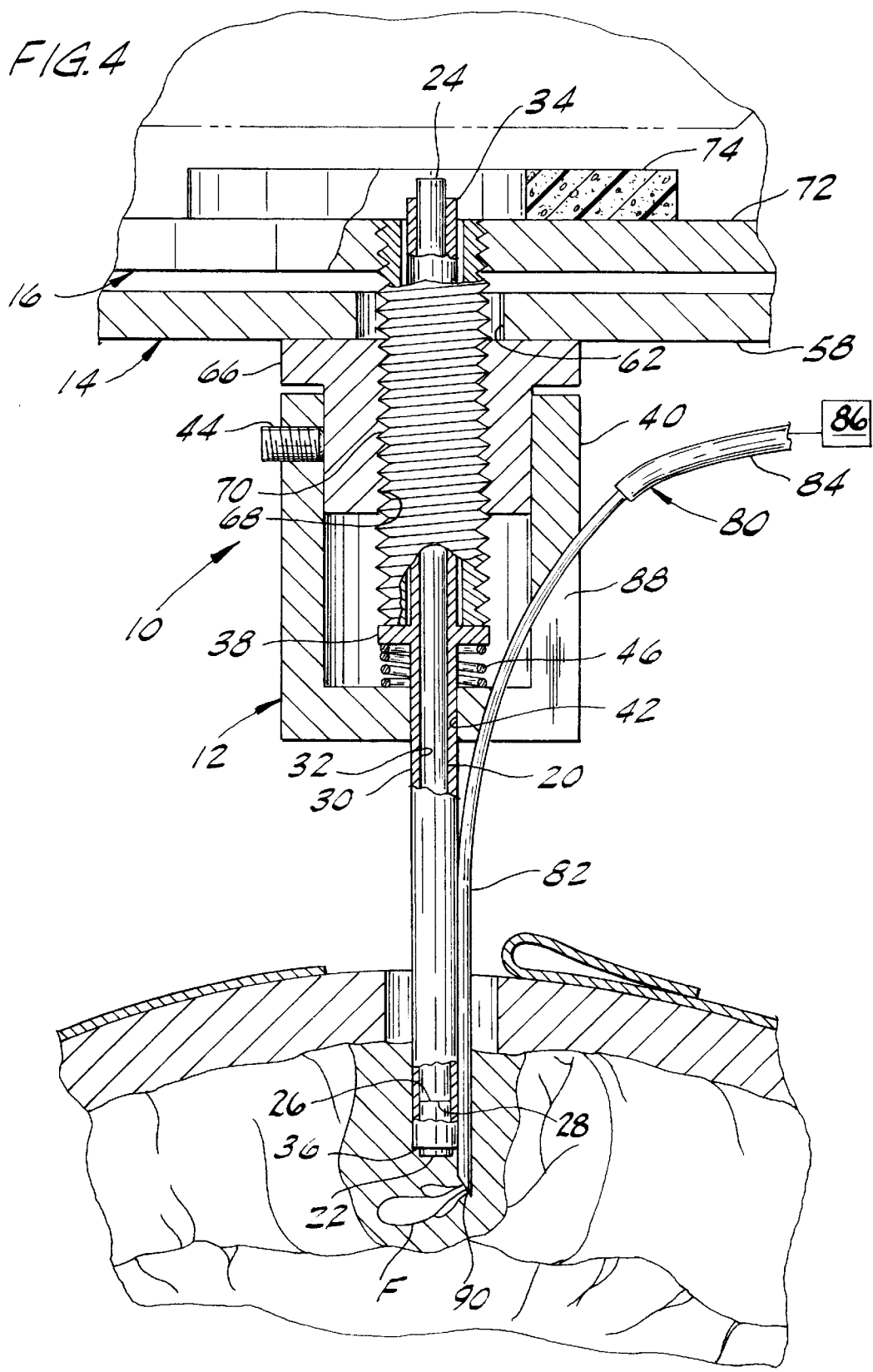
FIG. 4 is a detailed cross section of the attachment shown introducing a fluid into a brain of a patient.

As shown in FIG. 4, a tube or sleeve 30 surrounds the microlens 20 to protect it from damage. The tube 30 has a hollow interior 32 extending downward from an upper end 34 to a tip 36 adjacent the front (lower) end 22 of the microlens 20. The tip 36 is sufficiently narrow (e.g., less than about 3 mm, and more preferably less than about 0.5 mm) to permit the tube 30 and microlens 20 to be inserted inside living tissue without severely damaging the tissue. Although other materials may be used without departing from the scope of the present invention, the tube of the preferred embodiment is an 18 gauge stainless steel tube. Alternatively, it is envisioned that the tube may be made of glass, plastic or other insulating material. The microlens 20 is adhesively bonded inside the hollow interior 32 of the tube 30 in the preferred embodiment, but it is envisioned that other means of attachment may be used and that the microlens 20 may be made removable from the hollow interior 32 of the tube 30 without departing from the scope of the present invention. The tube 30 includes a radial flange forming a collar 38 about midway between the upper end 34 and the tip 36 for engaging the focusing mechanism 16 as will be explained in further detail below. The tube 30 is held by a thimble-shaped connector 40 having a central opening 42 which slidably receives the tube. The connector 40 includes a set screw 44 for joining the connector to the mount 14. A spring 46 surrounds the tube 30. The upper end of the spring 46 abuts the collar 38 and lower end of the spring rests against the inside of the bottom of the connector 40 to bias the tube 30 upward toward an objective O of the microscope and against the focusing mechanism 16.

Figure 2:
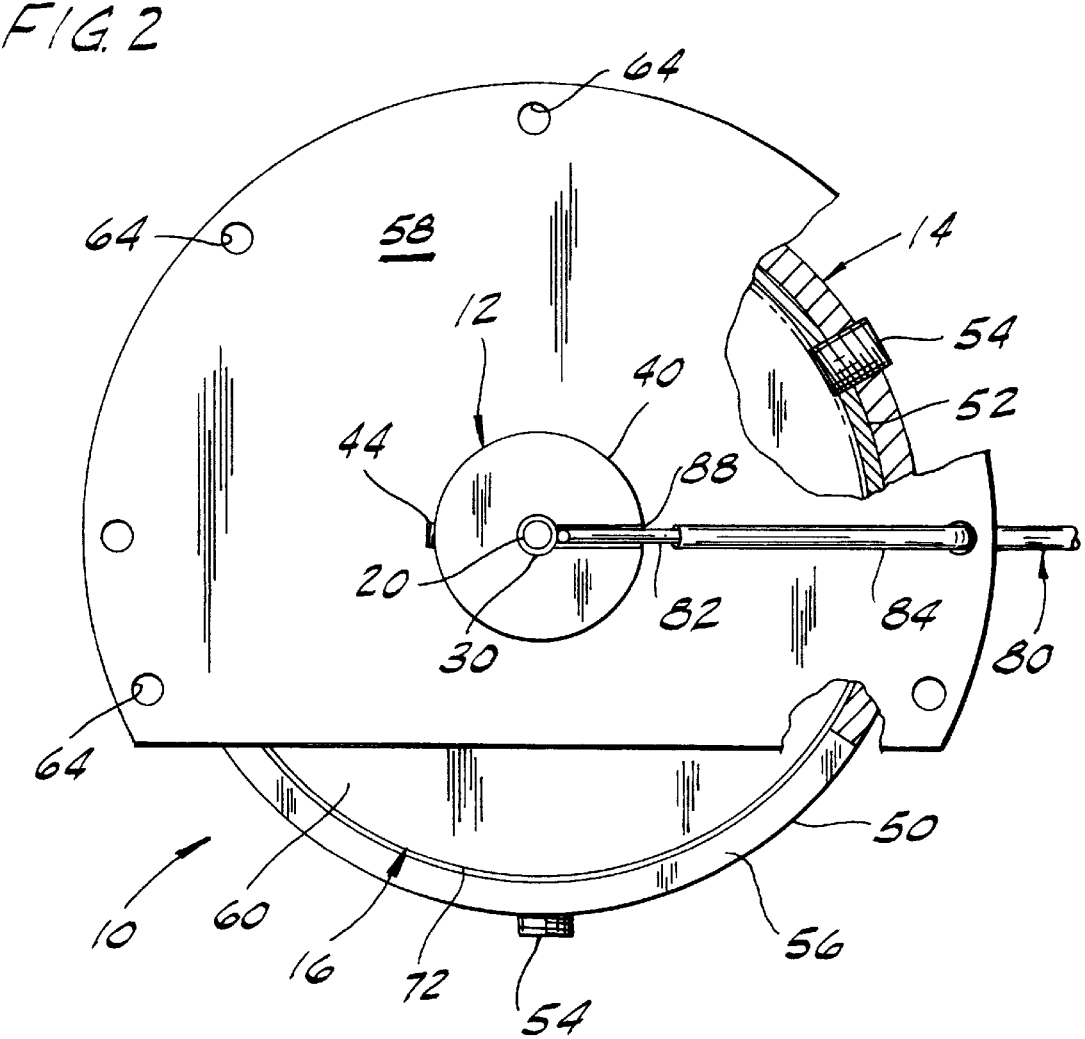
FIG. 2 is a bottom plan of the attachment in partial section.

As illustrated in FIG. 1, the mount 14 includes a cylinder 50 having an inner sleeve 52 sized for receiving a microscope objective O (shown in phantom in FIG. 1). It is envisioned that sleeves 52 having differing inner diameters may be provided to accommodate different microscope objectives O. Set screws 54 extending through the cylinder 50 and sleeve 52 engage the objective O to releasably mount the attachment 10 on the microscope. These screws 54 may have soft tips (e.g., Teflon® polymer tips) to avoid marring the objective O. (Teflon is a federally registered trademark of E.I. duPont de Nemours and Company.) As shown in FIGS. 1 and 2, an opening 56 is provided in the side of the cylinder 50 for accessing the focusing mechanism 16 as will be explained below. An end wall 58 extends across the bottom of the cylinder 50 to form the lower end of the mount 14. The wall 58 has an open segment 60 aligned with the opening 56 in the side of the cylinder 50 for providing additional access to the focusing mechanism 16. In addition, the wall 58 has a central aperture 62 (FIG. 1) for receiving a portion of the focusing mechanism 16 and one or more peripheral openings 64 for receiving ancillary systems which are used in combination with the attachment 10. As illustrated in FIG. , a lug 66 extends down from the end wall 58 below the central aperture 62 for engagement by the connector 40 when connecting the lens assembly 12 to the mount 14. A threaded hole 68 extends vertically through the lug 66 for receiving the focusing mechanism 16.

The focusing mechanism 16 includes a tubular adjustment screw 70 having a thumb wheel 72 at its upper end. The screw 70 extends downward through the threaded hole 68 of the lug 66 and engages the collar 38 on the tube 30 surrounding the microlens 20. As will appreciated by those skilled in the art, when the thumb wheel 72 is turned, the screw 70 rotates and moves either up or down with respect to the mount 14. Because the lower end of the screw 70 engages the collar 38 of the microlens 20, the lens assembly 12 also moves up or down along a longitudinal axis A of the microlens 20 but does not rotate. Therefore, rotation of the screw 70 effects vertical axial translation of the microlens 20 with respect to the objective O without rotating the tube 30 with respect to the mount 14. An annular pad 74 attached to the upper side of the thumb wheel 72 protects the microscope objective O from damage when the attachment 10 is mounted on the objective and when the focusing mechanism 16 is adjusted. Since the position of the microlens 20 may be adjusted independently of the mount 14, the microlens may be focused so that the image plane IP of the microlens corresponds with the focal plane of the microscope objective O. Further, the microlens 20 may be focused without moving the mount 14 relative to the objective O. As a result, the microlens 20 may be focused with respect to the objective O and the microlens may be moved to the precisely desired site in the tissue without affecting the focus. Further, both these adjustments may be performed without changing the position of the mount 14 on the objective O.

As previously mentioned, the attachment 10 may also include ancillary systems. For instance, the attachment 10 may have one or more fluid delivery systems, generally designated by 80 in FIG. 4. Each fluid delivery system 80 comprises a micropipette 82 and flexible tubing 84 sized for receiving an inlet end of the micropipette. An upstream end of the tubing 84 is connected to a fluid source 85 and the downstream end is connected to the micropipette 82. The tubing 84 extends through one of the peripheral openings 64 in the mount 14 to hold the tubing in position. As shown in FIG. 2, a slot 88 may be provided in the connector 40 for holding the micropipette 82 in position with respect to the lens assembly 12. Although other means of attachment are envisioned as being within the scope of the present invention, the micropipette 82 of the preferred embodiment is adhesively bonded to the outside of the lens assembly tube 30. As will be appreciated by those skilled in the art, the micropipette 82 is somewhat compliant so it can bend as shown in FIG. 1. In addition, the flexibility of the tubing 84 permits the tubing to follow the micropipette 82 as the focusing mechanism 16 moves the microlens 20 up or down with respect to the mount 14. The outlet end 90 of the micropipette 82 is positioned adjacent the front end 22 of the microlens 20. Moreover, the outlet end 90 is angled as shown in FIG. 1 to direct fluid F (FIG. 4) toward the field of view of the microlens 20 and to provide a pointed tip for improving the ease with which the attachment 10 may be advanced into tissue. The fluid delivery system 80 may be used to deliver a preselected amount of fluid F to a desired site within the field of view of the microlens 20. For instance, a liquid medicant can be injected into the tissue so its effects can be studied through the microscope, or a stain can be applied to the tissue to improve the contrast of features of the tissue. In addition, more than one fluid delivery system 80 may be coupled with the attachment 10 for delivering more than one fluid to the site.

Figure 5:
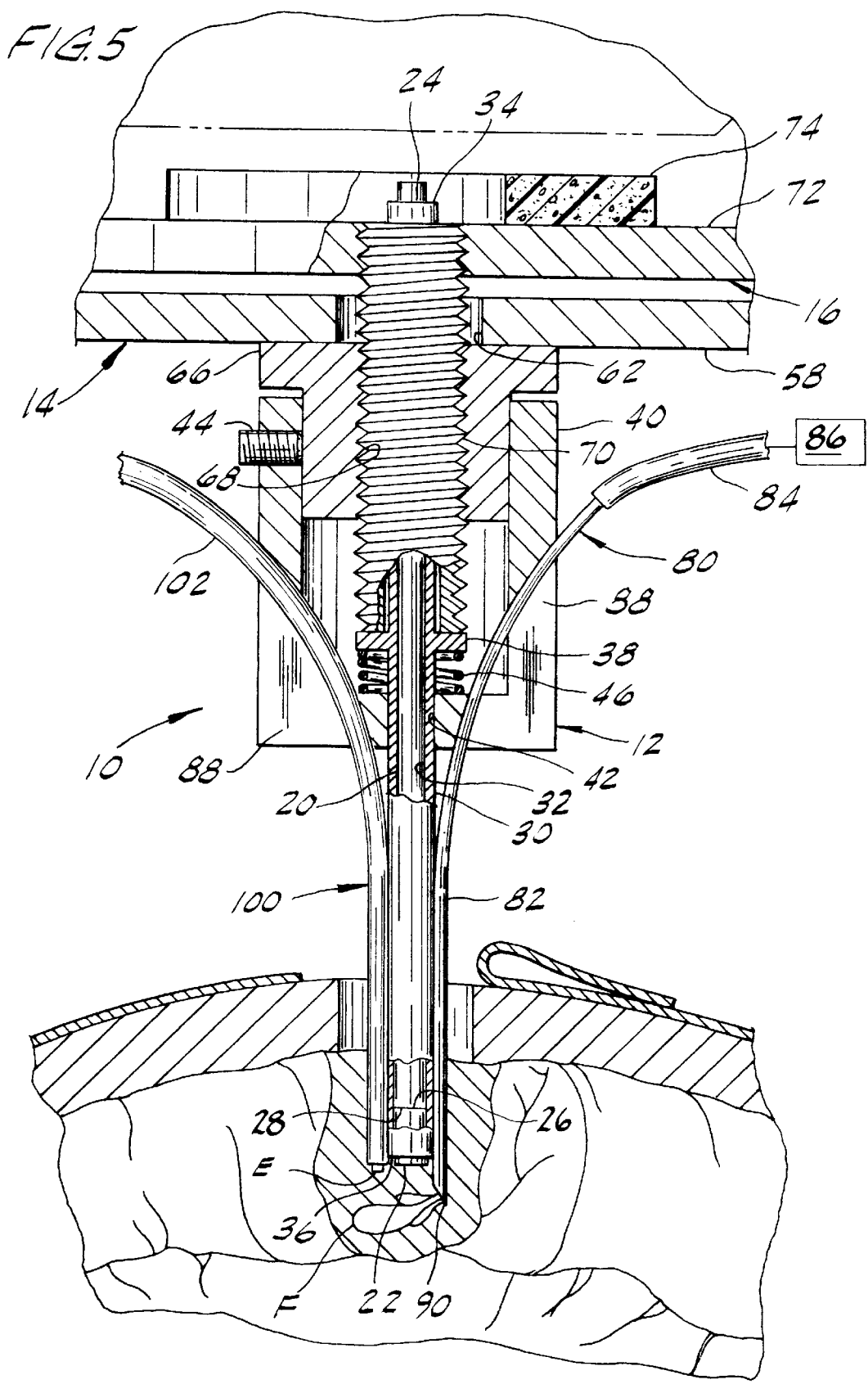
FIG. 5 is a detailed cross section of a second embodiment of the attachment shown guiding an instrument into a brain of a patient.

Other ancillary systems are also envisioned. For example, as shown in FIG. 5, the attachment 10 may include an instrument guidance system, generally designated 100, for guiding instruments (e.g., an electrode E) toward the site adjacent the front end 22 of the microlens 20. Although other configurations are envisioned as being within the scope of the present invention, the instrument guidance system 100 shown in FIG. 5 comprises flexible tubing 102 adhesively bonded to the outside of the lens assembly tube 30. The tubing 102 extends upward through a slot 88 provided in the connector 40. In addition, the tubing 102 may extend through one of the peripheral opening 64 in the mount 14 to hold the tubing in position. Depending upon the particular instrument intended to be carried by the tubing, the diameter of the tubing may vary. Because the lens assembly 12 does not rotate as the focusing mechanism 16 is adjusted, the angular position of the ancillary systems does not change with respect to the microlens 20 as the microlens is focused. As a result, the ancillary systems do not become twisted around the lens assembly 12 as the microlens 20 is focused.

Figure 3:
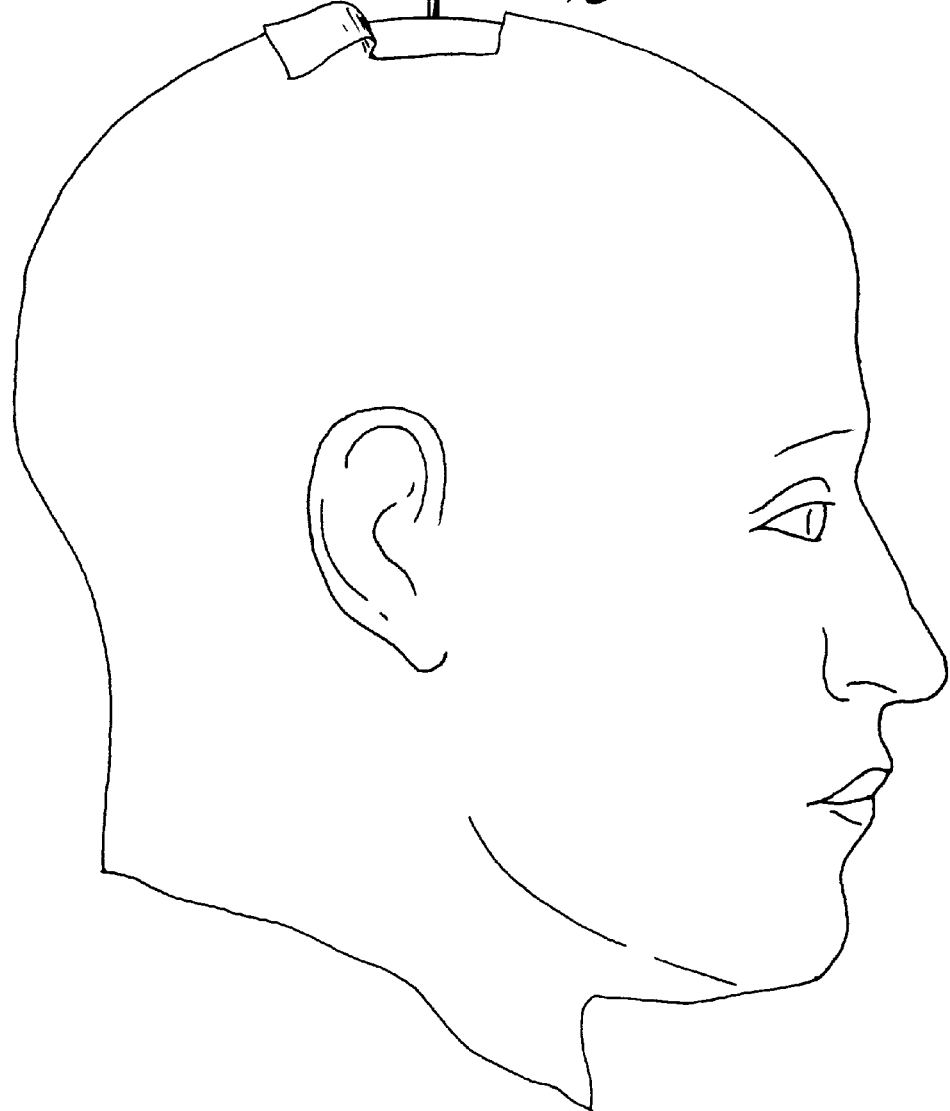
FIG. 3 is an elevation of the attachment shown inserted into a brain of a patient.

The attachment 10 of the present invention is used to view a desired site in living tissue of a host organism as shown in FIG. 3. The site is prepared by making an incision in the skin and soft tissue of the organism and removing any bone in a conventional manner. The mount 14 is positioned on a microscope objective O and the screws 54 are tightened to hold the mount in place. Once the screws 54 are tightened, the focusing mechanism 16 is adjusted by turning the thumb wheel 72 so the image plane IP of the microlens 20 corresponds with the focal plane of the microscope objective O. After the microlens 20 is focused, the microscope stage (not shown) may be adjusted to move the microlens and the objective O as a unit until the site on the living tissue lies within the field of view of the microlens at its focal plane FP. A guide needle (not shown) can be advanced in front of the microlens 20 to allow easier penetration of dense tissue. Ancillary systems may be used to introduce fluids or guide instruments to the site.

As will be appreciated by those skilled in the art, the attachment 10 of the present invention allows use of the microscope focusing mechanism (not shown) to micromanipulate the attachment into position. Further, the attachment 10 allows sites on both the exterior and interior of the tissue to be viewed while the tissue remains in the organism. Because the fluid delivery system directs fluid to the specific site of interest, small amounts of fluid, which are effective at the site but non-toxic to tissue surrounding the site, can be used. Moreover, the lens assembly 12 may be removed from the attachment 10 to change lens elements. Because the lens assembly 12 is removable, it may be discarded after use to prevent infecting others with infectious diseases (e.g., Jacob-Creutzfelt disease) which may be present in the tissue.

As will be further appreciated by those skilled in the art, the attachment 10 of the present invention is particularly useful when used with a conventional confocal optical microscope (e.g., a single or dual photon confocal microscope) as described in the Background of the Invention so light is directed from a light source 104 (FIG. 3) through the microlens 20 to illuminate the specimen. Because a confocal microscope does not require external lighting, only a small opening (about the size of the tube 30) need be made in the tissue to accommodate the attachment 10. Thus, the tissue is subjected to less mechanical and optical trauma than it would otherwise be. The image of the illuminated specimen is transmitted back through the microlens 20 to the image plane IP of the microlens. Because the image plane IP of the microlens 20 corresponds to the focal plane of the objective O, the microscope magnifies the image so cells and other structures in the tissue may be viewed. Moreover, because light can be transmitted through several hundreds of microns of tissue and the focal plane FP of the microlens 20 can be positioned below the surface of the tissue, the attachment 10 may be used to view sub-surface portions of the tissue such as the extracellular matrix, the cells and the intracellular matrix. Further, the attachment 10 may be used to view the matrices and cellular membranes without penetrating and thereby damaging the extracellular matrix. For example, as the attachment 10 of the present invention is inserted into the extracellular matrix, arteries ahead of the microlens 20 can be viewed so the user can alter the path of the attachment as it is advanced before causing permanent and irreversible global tissue damage (e.g., brain herniation from intracranial hemorrhage). Those skilled in the art will further appreciate that the attachment 10 of the present invention may be used with a conventional epiflourescence microscope.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. An assembly for viewing cells inside tissue of a living organism, the assembly comprising:

a confocal microscope having an objective for magnifying an image positioned at a focal plane of the objective and a light source adapted to direct light through the objective;

a rigid elongate tube extending from adjacent the objective to a tip adapted for penetrating the tissue of the living organism to position the tip adjacent cells inside the tissue, the tube having a hollow interior aligned with the objective for directing light from the light source to cells inside the tissue of the living organism adjacent the tip, the interior of the tube being free of fiberoptic bundles; and a lens positioned in the hollow interior of the tube for transmitting light from the light source to the cells inside the tissue of the living organism adjacent the tip to illuminate the cells, the lens having a focal plane adjacent the tip positioned at a location corresponding to the illuminated cells and an image plane opposite the tip, and a focusing mechanism for moving the tube and lens relative to the objective along a longitudinal axis of the tube to position the lens so that the image plane of the lens corresponds with the focal plane of the objective thereby permitting the cells inside the tissue of the living organism to be viewed with the microscope.

2. An assembly as set forth in claim 1 further comprising a fluid delivery system mounted on the tube for delivering fluid to cells adjacent the tip.

3. An assembly as set forth in claim 2 wherein said fluid delivery system comprises a micropipette having an inlet end connected to a fluid source and a pointed outlet end extending beyond the tip of the said tube.

4. An assembly as set forth in claim 1 further comprising an instrument guidance system mounted on the tube for guiding instruments toward a site in the tissue adjacent the tip.

5. An assembly as set forth in claim 4 wherein the instrument guidance system comprises a guide extending adjacent said tube sized and shaped for guiding at least a portion of an instrument toward the site in the tissue.

6. An assembly as set forth in claim 1 wherein the lens is removable from the hollow interior of the tube.

7. An assembly as set forth in claim 1 wherein said lens has a longitudinal axis and is mounted for movement along said axis with respect to the microscope objective so that the image plane of the lens is moveable to a position corresponding with the focal plane of the microscope objective.

8. An assembly as set forth in claim 7 wherein said lens is mounted for movement along said axis without rotation about said axis.

9. An assembly as set forth in claim 7 wherein said focusing mechanism comprises an adjustment screw rotatable for moving the tube and lens with respect to the microscope objective.

10. An assembly as set forth in claim 9 wherein the adjustment screw is rotatable to effect translation of the lens with respect to the objective without rotating the tube with respect to the objective.

11. An assembly as set forth in claim 10 further comprising a mount for mounting the tube and lens on the microscope, said adjustment screw being mounted for rotation relative to the mount, and said focusing mechanism further comprising a spring on the mount for biasing the tube and lens toward the microscope objective.

12. An assembly as set forth in claim 1 wherein the lens has an outside diameter substantially equal to an inside diameter of the tube.

13. An attachment for use with a microscope having objective, said attachment comprising:

a rigid elongate tube having a hollow interior extending to a tip having a width of less than about three millimeters to permit the tip to be inserted into tissue of a living organism;

a lens positioned in the hollow interior of the tube for transmitting an image of a specimen positioned at a focal plane of the lens adjacent a front end thereof to an image plane of the lens adjacent a rear end of the tube;

a mount for mounting the tube and lens on a microscope, and a focusing mechanism on the mount for moving the tube and lens relative to the objective along a longitudinal axis of the tube to position the lens so that the image plane of the lens corresponds with the focal plane of the objective thereby permitting cells inside the tissue of the living organism to be viewed with the microscope.

14. An attachment as set forth in claim 13 wherein the lens includes an objective lens and a relay lens.

15. An attachment as set forth in claim 13 wherein said focusing mechanism comprises an adjustment screw rotatable in the mount for moving the tube and lens with respect to the microscope objective.

16. An attachment as set forth in claim 15 wherein the adjustment screw is rotatable to effect translation of the lens with respect to the objective without rotating the tube with respect to the objective.

17. An attachment as set forth in claim 16 wherein said focusing mechanism further comprising a spring on the mount for biasing the tube and lens toward the microscope objective.

18. An attachment as set forth in claim 13 further comprising a fluid delivery system mounted on the tube for delivering fluid to cells adjacent the tip, said fluid delivery system comprising a micropipette having an inlet end adapted for connection to a fluid source and a pointed outlet end extending beyond the tip of the said tube.

19. An attachment as set forth in claim 13 wherein the lens is adapted for transmitting light from a light source to illuminate cells inside said tissue.

20. An attachment as set forth in claim 19 wherein the interior of the tube is free of fiberoptic bundles.

21. An attachment as set forth in claim 20 wherein the lens has an outside diameter substantially equal to an inside diameter of the tube.

22. A method of viewing cells inside tissue of living organisms comprising the steps of:

mounting a cylindrical lens inside a tube adjacent an objective of a microscope;

adjusting the lens by moving the tube and lens relative to the objective so that an image plane of the lens corresponds with a focal plane of the microscope objective; and while maintaining the tube, lens and objective in fixed position relative to one another, effecting relative movement between the tissue, on the one hand, and the tube, lens and objective, on the other hand, to penetrate the tissue with the tube and to position the lens so the cells lie within a focal plane of the lens.

23. A method as set forth in claim 22 wherein the lens is moved so the cells lying in the focal plane of the lens are separated from the lens by cells lying between the lens and the focal plane of the lens.

24. A method as set forth in claim 22 further comprising the step of introducing a fluid to the cells in an amount which is non-toxic to tissue surrounding the cells.

25. A method as set forth in claim 22 further comprising the steps of introducing a medicant to the cells and observing a response to the medicant.

26. A method as set forth in claim 25 wherein the medicant is introduced in an amount sufficiently small to minimize its affect on tissue surrounding the cells.

27. A method as set forth in claim 22 further comprising the step of introducing a stain to the cells in an amount sufficiently small to minimize its affect on tissue surrounding the cells.

28. A method as set forth in claim 22 wherein said relative movement is effected by moving the tissue relative to the tube, lens and objective.

* * * * *